(12) United States Patent
Kim

(10) Patent No.: US 11,583,271 B2
(45) Date of Patent: Feb. 21, 2023

(54) MEDICAL THREAD BASED ON ULTRASONIC PRODUCTION

(71) Applicant: MEDI FUTURES CO., LTD., Seongnam-si (KR)

(72) Inventor: Ji Hwan Kim, Busan (KR)

(73) Assignee: MEDI FUTURES CO., LTD., Seongnam-si (KR)

( * ) Notice: Subject to any disclaimer, the term of this patent is extended or adjusted under 35 U.S.C. 154(b) by 0 days.

(21) Appl. No.: 16/479,028

(22) PCT Filed: Sep. 4, 2018

(86) PCT No.: PCT/KR2018/010296
§ 371 (c)(1),
(2) Date: Jul. 18, 2019

(87) PCT Pub. No.: WO2019/132164
PCT Pub. Date: Jul. 4, 2019

(65) Prior Publication Data
US 2021/0259686 A1 Aug. 26, 2021

(30) Foreign Application Priority Data

Dec. 28, 2017 (KR) .................. 10-2017-0183108
Jun. 7, 2018 (KR) .................. 10-2018-0065469
Aug. 31, 2018 (KR) .................. 10-2018-0103672

(51) Int. Cl.
*A61B 17/06* (2006.01)
*A61B 17/00* (2006.01)

(52) U.S. Cl.
CPC .............. *A61B 17/06166* (2013.01); *A61B 2017/00526* (2013.01); *A61B 2017/0619* (2013.01); *A61B 2017/06176* (2013.01)

(58) Field of Classification Search
CPC .... A61B 17/06166; A61B 2017/06176; A61B 2017/0619; A61B 2017/00955;
(Continued)

(56) References Cited

U.S. PATENT DOCUMENTS 8,771,313 B2   7/2014   Goraltchouk et al.
8,888,810 B2   11/2014  Hadba et al.
(Continued)

FOREIGN PATENT DOCUMENTS

JP      5649776 B2     1/2015
JP    2017094116 A     6/2017
(Continued)

OTHER PUBLICATIONS

European Search Report of EP Application No. 18894277.5 dated May 10, 2021.
(Continued)

*Primary Examiner* — Kathleen S Holwerda
*Assistant Examiner* — Lauren Dubose
(74) *Attorney, Agent, or Firm* — Dinsmore & Shohl LLP

(57) ABSTRACT

According to the aspect of the present disclosure, various forms of medical 3D threads produced using ultrasonic waves are provided. Thus, we can expect high satisfaction with the medical 3D threads having high tensile strength and holding power. The medical 3D threads can be produced to have about twice as many barbs as conventional medical threads and can be produced using ultrasonic waves without damaging yarn or making knots. Thus, it is possible to overcome the cause of a decrease in physical strength.

6 Claims, 11 Drawing Sheets

(58) Field of Classification Search
CPC ...... A61B 2017/00526; A61B 2017/00579; A61B 2017/0649; A61B 17/04–17/062; A61B 2017/00884; A61F 2220/0016
See application file for complete search history.

(56) References Cited

U.S. PATENT DOCUMENTS

| | | |
|---|---|---|
| 2003/0149447 A1 | 8/2003 | Morency et al. |
| 2004/0060409 A1* | 4/2004 | Leung ............... A61B 17/04 83/522.14 |
| 2010/0146770 A1 | 6/2010 | Morency et al. |
| 2018/0177505 A1* | 6/2018 | Chu ............... A61B 17/06166 |

FOREIGN PATENT DOCUMENTS

| | | | |
|---|---|---|---|
| KR | 200353217 Y1 | 6/2004 | |
| KR | 101132841 B1 | 4/2012 | |
| KR | 1020140076063 A | 6/2014 | |
| KR | 101432497 B1 | 8/2014 | |
| KR | 1020140147683 A | 12/2014 | |
| WO | WO-2014204135 A1 * | 12/2014 | ............. A61B 17/04 |

OTHER PUBLICATIONS

International Search Report for PCT/KR2018/010296 dated Nov. 30, 2018.

* cited by examiner

MEDICAL THREAD BASED ON ULTRASONIC PRODUCTION

This application is a national stage of International Application No. PCT/KR2018/010296 filed on Sep. 4, 2018, which claims priority to Korean Patent Application No. 10-2017-0183108 filed on Dec. 28, 2017, Korean Patent Application No. 10-2018-0065469 filed on Jun. 7, 2018, and Korean Patent Application No. 10-2018-0103672 filed on Aug. 31, 2018, the entire contents of which are herein incorporated by reference.

TECHNICAL FIELD

The present disclosure relates to a medical 3D thread produced using ultrasonic waves, and more particularly to a medical 3D thread that is produced by applying ultrasonic waves to a suture which has been used for beauty and medical use to have a delicate form and various forms suitable for use.

BACKGROUND

Conventionally, medical threads have been used mainly for suturing in surgery, and suturing has been used to lift up sagging skin and tissues of the face, chin, neck, abdomen, vagina, breast, or hip by using needles and threads instead of using a scalpel and also used to tighten and smooth wrinkles. The suturing has attracted much attention because it does not excessively incise the skin, minimizes scarring, and reduces bleeding and swelling caused by surgery.

The medical threads may be formed using natural materials and synthetic materials, and natural material-based absorbable medical threads have been formed of catgut, chromic, gut, or the like and synthetic material-based absorbable medical threads have been formed of polyglycolic acid (Dexon, Mexon), polyglactin (Vicryl), and polydioxanone (PDS). The natural material-based absorbable medical threads may also be formed of silk, and the synthetic material-based absorbable medical threads may also be formed of polyester (Dacron), polypropylene (Proline), polyamide (Nylon), and e-PTFE (Gore-Tex).

Conventionally, medical threads including barbs on the surface have been used. In a conventional production method, the medical threads have been produced by thermoforming or compression, and, thus, the threads have uneven surface or have been limited in having a delicate form. The medical threads have had lint around the bars. Also, due to the properties of polydioxanone (PDO), deformation occurs and the strength decreases during thermoforming.

DISCLOSURE OF THE INVENTION

Problems to be Solved by the Invention

To solve the above-described conventional problem, the present disclosure provides a medical 3D thread produced using ultrasonic waves.

The present disclosure provides a medical 3D thread produced using an ultrasonic generator to provide a medical thread (suture) that can be transformed into a more delicate form than conventional medical threads (sutures) and overcomes the cause of a decrease in physical strength and includes barbs having a thickness or length controlled precisely to 2 decimal places.

Means for Solving the Problems

To achieve the above-described problems, a medical 3D thread produced using ultrasonic waves according to a first aspect of the present disclosure includes a body part which serves as a central axis of the 3D thread and has a thickness of from 0.2 mm to 0.6 mm and multiple barb parts formed and extended from both lateral sides of the body part, and barbs of the multiple barb parts have a protruded width of from 0.05 mm to 0.5 mm based on the body part and has the greatest thickness of from 0.1 mm to 0.6 mm and a length of from 1.0 mm to 1.4 mm in an extension direction of the body part.

Further, a medical thread according to a second aspect of the present disclosure includes: a body portion including a trench which is recessed in the middle of a lower surface in a long-side length direction; and multiple barb parts formed and protruded from both sides of the trench.

A medical thread according to a third aspect of the present disclosure includes: a body portion extended in one direction; a stop member provided on one end of the body portion and formed to have a greater width than the body portion; and multiple barb parts formed and protruded from at least one surface of the body portion.

Effects of the Invention

According to the first aspect of the present disclosure, various forms of medical 3D threads produced using ultrasonic waves are provided. Thus, we can expect high satisfaction with the medical 3D threads having high tensile strength and holding power.

The medical 3D threads can be produced to have about twice as many barbs as conventional medical threads and can be produced using ultrasonic waves without damaging yarn or making knots. Thus, it is possible to overcome the cause of a decrease in physical strength.

Therefore, the medical 3D threads can be expected to be more effective in skin lifting surgery and can provide stronger fixing and holding than conventional products.

A cog shape or various 3D shapes can be prepared by applying ultrasonic vibration to a material and putting particles of the material in an ultrasonic mold, as compared to a method of cutting a thread with heat and pressure of a mold.

Conventionally, a thread is applied with heat and flattened with a roller and then applied with pressure of a mold and cut into the shape of the mold, and, thus, a material of the thread is increased in volume and density and the properties of the material are degraded by about 30% and if the flattened thread expanded by heat is pressed and cut by a cog-shaped mold, the ends of cogs have lint and thus cannot be pointed. However, according to a method of producing a thread using ultrasonic vibration, a thread put in a cog-shaped mold is applied with minimized heat or artificial stimulus for a short time, and, thus, a material of the thread is almost not degraded and can maintain the existing strength and properties.

According to the second aspect of the present disclosure, the trench is formed in the longitudinal direction to increase a contact area with the skin and thus improve the fixation power with the skin. Therefore, it is possible to suppress the deviation of the medical thread from where the medical thread is initially buried. For example, if the medical thread is inserted to improve wrinkles on the forehead, when the patient frowns after surgery, the medical thread may deviate from its initial location. If the medical thread has a trench (tunnel) or barbs as in the present disclosure, it is possible to effectively suppress the deviation of the medical thread.

Particularly, if the multiple barbs are separated to form a space, the fixation power with the skin can be further improved. Additionally, a space where a filler can be introduced may be formed in the trench.

Further, the 3D thread according to the present disclosure can be produced only by ultrasonic processing. In a conventional method, a medical thread is produced by compressing yarn and pressing the yarn in a mold or cutting yarn to form barbs. Therefore, it is impossible to produce a delicate 3D trench structure provided by the present disclosure.

The medical thread according to the present disclosure can be used as a suture for tissues (e.g., skin, muscles, body organs, etc.). When it is used as a suture, it can provide much more convenience and efficiency in making a knot than conventional sutures.

BEST MODE FOR CARRYING OUT THE INVENTION

Figure 1:
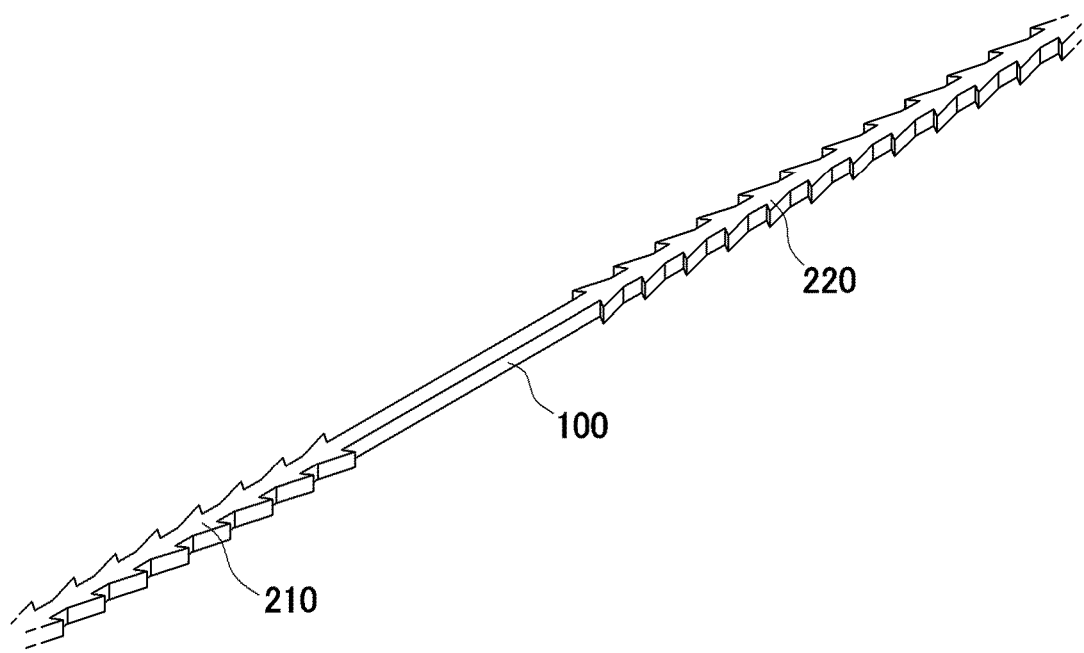
FIG. 1 is a perspective view of a medical 3D thread according to a first example of the present disclosure.

The present disclosure may have various modifications imposed thereto and implemented in various embodiments, and thus embodiments (or examples) will be described in detail in the best mode. However, it should be understood that the present disclosure is not intended to limit to those particular embodiments, and the present disclosure may encompass any modifications, equivalents, and alternatives embraced by the spirit and the technical scope of the present disclosure.

Through the whole document, the term "connected to" or "coupled to" that is used to designate a connection or coupling of one element to another element includes both a case that an element is "directly connected or coupled to" another element and a case that an element is "electronically connected or coupled to" another element via still another element. Further, it is to be understood that the term "comprises or includes" and/or "comprising or including" used in the document means that one or more other components, steps, operation and/or existence or addition of elements are not excluded in addition to the described components, steps, operation and/or elements unless context dictates otherwise.

Also, the components in each drawing may be expressed exaggeratingly larger (or thicker) or smaller (or thinner) in size or thickness, or by simplified structure thereof for the sake of convenience of understanding, but it should not be construed the scope of the protection of the present disclosure is limited thereby.

Further, the shapes or forms of the components in each drawing are shown to explain embodiments of the present disclosure, but do not limit the present disclosure.

The terms used herein are used only to describe specific embodiments (or examples), but do not intend to limit the present disclosure. A singular expression includes a plural expression unless it is clearly construed in a different way in the context. The terms used herein, such as "including" or "having", are used only to designate the features, numbers, steps, operations, constituent elements, parts, or combinations thereof described in the specification, but should be construed not to exclude existence or addition of one or more other features, numbers, steps, operations, constituent elements, parts, or combinations thereof.

Unless otherwise defined, all terms including technical and scientific terms used herein have the same meaning as commonly understood by a person with ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein.

Further, the present disclosure will be described in detail with reference to first to third examples.

Hereafter, a medical 3D thread produced using ultrasonic waves according to a first example of the present disclosure will be described in detail with reference to FIG. 1 and FIG. 2.

The medical 3D thread produced using ultrasonic waves according to the first example of the present disclosure may include a body part 100 and a first barb set 210 and a second barb set 220 formed and extended from both lateral sides of the body part.

Yarn for producing the medical 3D thread is thermoplastic resin, and the medical 3D thread is produced using ultrasonic waves. Polydioxanone (PDO) which has been typically used has a melting point of 106° C., and when reaching the melting point, PDO may be deformed and reduced in tensile strength and holding power.

The ultrasonic waves used for production have a frequency of from 2 kHz to 3 kHz and generate heat whose temperature is lower than the melting point of the yarn. Desirably, the ultrasonic waves may generate heat only to cause deformation with a frequency of 2.5 kHz.

The yarn located between an ultrasonic generator and a mold base adjacent to each other is inserted into a location corresponding to an engraved pattern of the mold base and applied with ultrasonic waves while being pressed by the ultrasonic generator, and a 3D thread formed into the shape of the engraved pattern can be produced using the ultrasonic waves.

The 3D thread may be formed including multiple barbs facing on both sides.

The ultrasonic generator may be provided on an upper end of a device for producing a 3D thread and may be spaced apart from the mold base fixed on the ground.

In this case, the ultrasonic generator and the mold base may be formed to have a flat-plate shape and may be arranged to share the central axis. That is, the ultrasonic generator and the mold base may share the same central axis and may be arranged in parallel in one direction.

When the yarn is inserted, the ultrasonic generator may generate ultrasonic waves while moving downwards so as to be in contact with the mold base and thus may apply the ultrasonic waves to the inserted yarn while pressing the inserted yarn.

The yarn is inserted through a yarn insertion part and inserted and fixed to a location corresponding to the engraved pattern of the mold base, and the width of the yarn may be greater than that of the engraved pattern.

When the yarn is located on the engraved pattern of the mold base, the above-described ultrasonic generator may operate and a 3D thread may be produced.

The body part 100 of the medical 3D thread includes spare parts 120 on its both ends and also include a center part 110 connecting the first barb set 210 and the second barb set 220, and the barbs are formed toward the center part.

Figure 2:
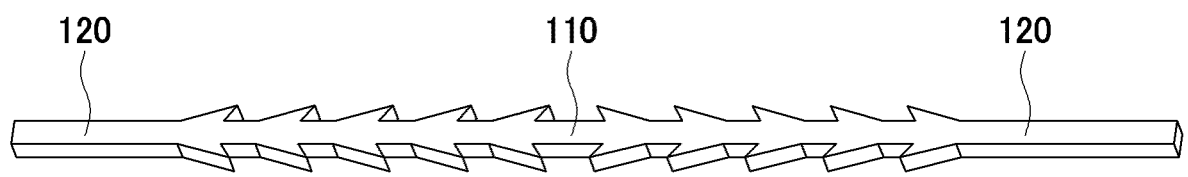
FIG. 2 is a perspective view of a medical 3D thread according to a first example of the present disclosure.

The thread illustrated in FIG. 1 and FIG. 2 has the shape of the medical 3D thread according to the first example of the present disclosure, but may have various shapes depending on the shape of the mold base used for production.

Hereafter, the medical 3D thread according to the present disclosure will be described with reference to FIG. 3.

If the length direction of the body part 100 of the medical 3D thread is defined as transverse direction and the width direction of the body part 100 is defined as longitudinal direction, a transverse section or longitudinal section of each barb may have a rectangular shape.

Figure 3:
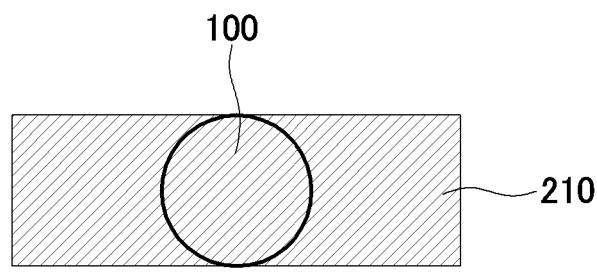
FIG. 3 is a longitudinal cross-sectional view of the medical 3D thread according to the first example of the present disclosure.

FIG. 3 is a longitudinal cross-sectional view of the medical 3D thread and illustrates that the body part 100 is formed at the center and barb parts are formed and extended therefrom. FIG. 3 illustrates a longitudinal cross-sectional view of where the first barb set 210 is located.

The angular portions, i.e., the ends, of the first barb set 210 and the second barb set 220 are formed to have a predetermined thickness as shown in FIG. 3. Thus, even if the ends of the bar sets are melted, the tensile force can be maintained without decrease or loss.

Figure 4:
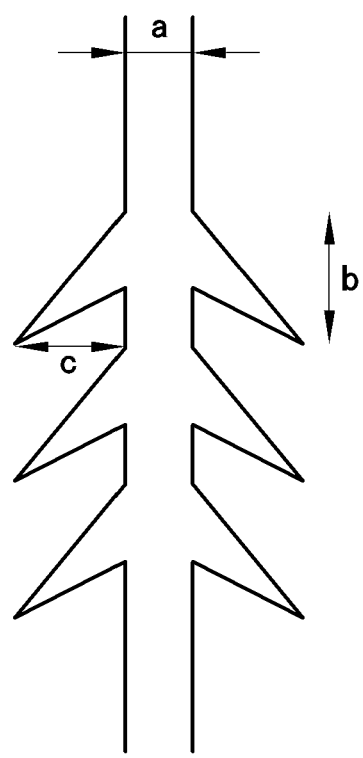
FIG. 4 is a perspective view provided to explain the width, thickness and length of the medical 3D thread according to the first example of the present disclosure.

FIG. 4 is a perspective view provided to explain the size of the medical 3D thread according to the first example of the present disclosure.

As illustrated in FIG. 4, a thickness a of the body part 100 may serve as the central axis of the medical 3D thread and may be in the range of from 0.2 mm to 0.6 mm. The thickness a of the body part 100 may be adjusted according to use.

The barb parts formed and extended from both lateral sides of the body part 100 may have a width c protruding from the body part 100 in the range of from 0.05 mm to 0.5 mm. The protruded barbs are extended from both lateral sides so as to correspond to each other, and may be symmetrically or alternately formed in pairs according to use.

Meanwhile, the barbs extended from the body part 100 may be formed to have a predetermined thickness and the greatest thickness of from 0.1 mm to 0.6 mm so as to correspond to the thickness of the body part.

The end of each barb heading toward the center part 110 of the body part 100, i.e., a length b in an extension direction of the body part 100, may be in the range of from 1.0 mm to 1.4 mm. The length b may be adjusted according to use.

Specifically, the 3D thread of the present disclosure and a 3D thread produced according to conventional technology can be compared as follows. The 3D thread of the present disclosure can be very delicately produced using ultrasonic waves and thus may have a smaller and more delicate pattern than the 3D thread produced according to conventional technology.

Hereafter, the medical 3D thread according to the first example of the present disclosure will be further described with reference to FIG. 5.

Figure 5:
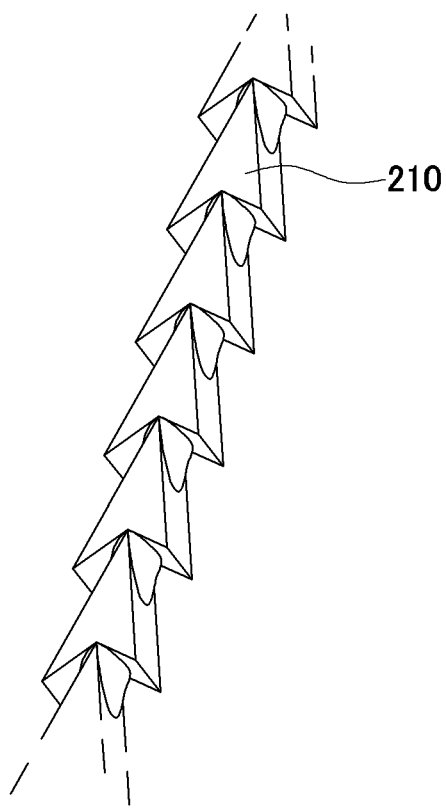
FIG. 5 is a side view of the medical 3D thread according to the first example of the present disclosure.

FIG. 5 shows the first barb set 210 in the medical 3D thread according to the first example of the present disclosure. As shown in FIG. 5, the barb part may be formed to have a predetermined thickness.

The medical 3D thread shown in FIG. 5 according to the first example includes barbs each having the thickness equal to the thickness of the body part 100, i.e., the diameter of the circular body part 100, and each barb may have the same thickness from where the barb starts from the body part 100 as the angular portion.

When viewed from the side, one lateral side of the barb has a rectangular shape with bilateral symmetry.

The barb is extended from the body part 100, and the barb according to the first example of the present disclosure has a triangular shape as shown in the drawing. An interior angle between the longest side of the barb and the body part 100 is an acute angle, and an interior angle between the shortest side of the barb and the body part 100 is an obtuse angle, and, thus, the barbs may head toward the center part 110.

In the medical 3D thread according to the first example of the present disclosure, the first barb set 210 and the second barb set 220 may have different lengths.

Hereafter, another example of the present disclosure will be described in detail with reference to FIG. 6 through FIG. 9D.

Figure 6:
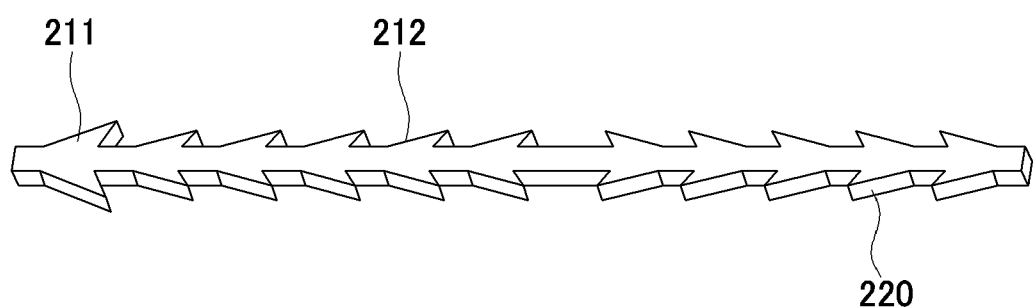
FIG. 6 is a perspective view of a form of the 3D thread according to the first example of the present disclosure.

FIG. 6 is a perspective view of a medical 3D thread according to an additional example of the present disclosure.

As in the first example, the medical 3D thread includes the first barb set 210 and the second barb set 220 formed and extended from the body part 100, and barbs of a 1st-1st barb part 211 adjacent to one end of the body part 100 among the plurality of barbs of the first barb set 210 may be formed to have a greater width than barbs of a 1st-2nd barb part 212 except the barbs of the 1st-1st barb part 211 and barbs of the second barb set 220.

For example, as shown in FIG. 6, barbs adjacent to one end of the 3D thread may be formed greater than the other barbs of the 3D thread so as to be easily accommodated in a storage container where the 3D thread is kept.

The 1st-1st barb part 211 is formed corresponding in width to an insertion opening of the storage container and exposed in part, which enables the 3D thread to easily come in and out. Further, the 1st-1st barb part 211 is not actually inserted into the body during surgery, and, thus, even if it is melted or not formed, the 3D thread can be used without any problem.

Further, the barbs of the 1st-1st barb part 211 may have a smaller thickness than the bars of the 1st-2nd barb part 212, and the body part without barbs may be formed on the other end of the 1st-2nd barb part 212, i.e., the end connected to the second barb part 220, and thus may serve as the center part 110 of the 3D thread according to the first example.

The body part without barbs may not be formed on the other end of the 1st-1st barb part 211 located farthest from the 1st-2nd barb part 212.

Figure 7:
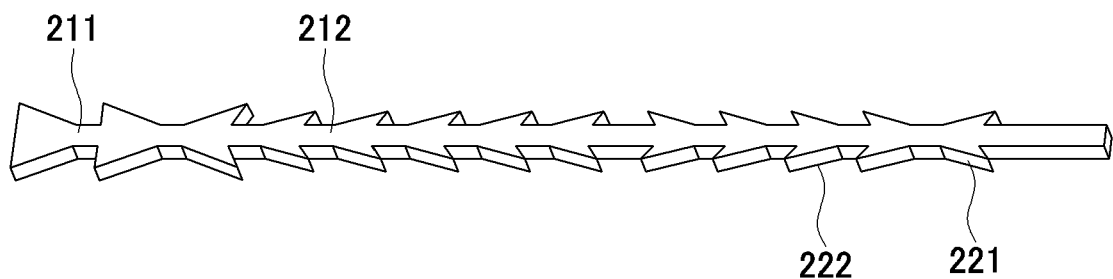
FIG. 7 is a perspective view of another form of the 3D thread according to the first example of the present disclosure.

FIG. 7 is a perspective view of a medical 3D thread according to an additional example of the present disclosure.

The medical 3D thread may include the first barb set 210 which includes first barb parts formed in one direction and the second barb set 220 which includes second barb parts formed in the opposite direction of the first barb parts and is spaced apart from the first barb set 210.

The first barb set 210 is formed on one end of the medical 3D thread, and the second barb set 220 and the body part 100 without barbs are formed on the other end of the medical 3D thread. The body part without barbs may be arranged last.

Among the first barbs included in the first barb set 210, barbs located farthest from the second barbs may be formed in the opposite direction of the other first barbs, and among the second barbs included in the second barb set 220, barbs located farthest from the first barbs may be formed in the opposite direction of the other second barbs.

That is, in the first barb set 210, the 1st-1st barb part 211 may include barbs formed in the opposite direction of the 1st-2nd barb part 212 heading toward the center part 110, and a 2nd-1st barb part 221 may include barbs formed in the opposite direction of a 2nd-2nd barb part 222 heading toward the center part 110.

However, as shown in FIG. 7, one or more pairs of barbs may be formed farthest from each barb set in the opposite direction of the other barbs of each barb set.

The body part 100 without barbs may be further formed on one end of the first barb set 210 (not illustrated).

Figure 8:
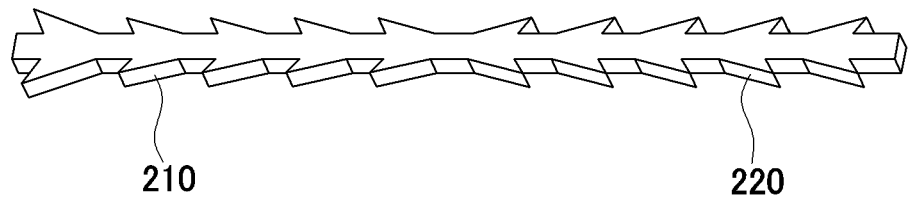
FIG. 8 is a perspective view of another form of the 3D thread according to the first example of the present disclosure.
Figure 9A:
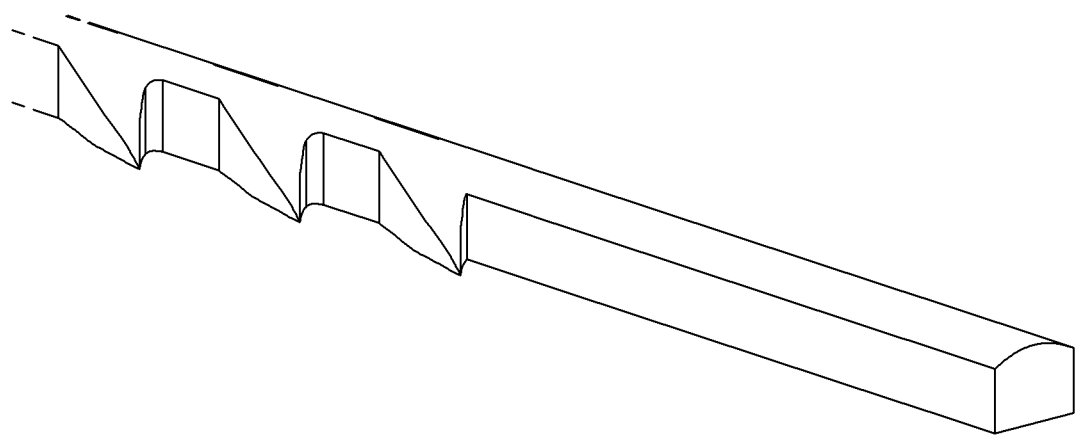
FIG. 9A is a perspective view of another form of the 3D thread according to the first example of the present disclosure.
Figure 9B:
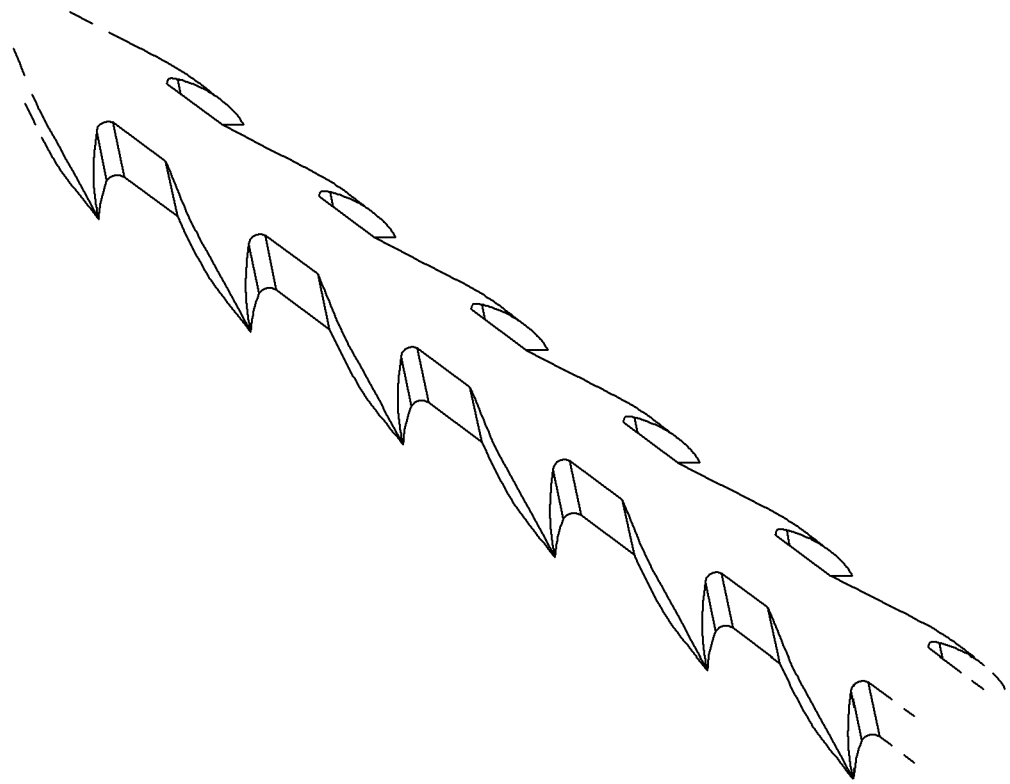
FIG. 9B is a perspective view of another form of the 3D thread according to the first example of the present disclosure.
Figure 9C:
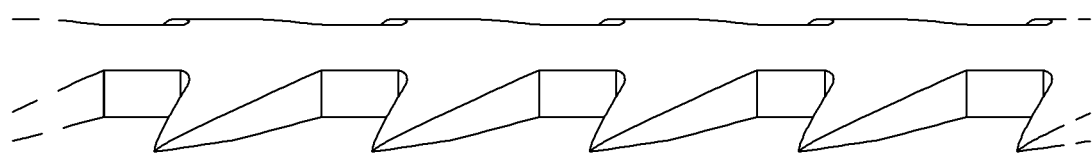
FIG. 9C is a perspective view of another form of the 3D thread according to the first example of the present disclosure
Figure 9D:
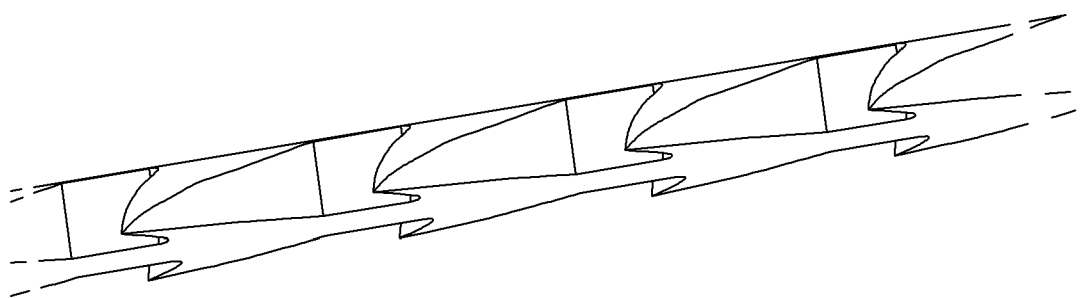
FIG. 9D is a perspective view of another form of the 3D thread according to the first example of the present disclosure
Figure 10:
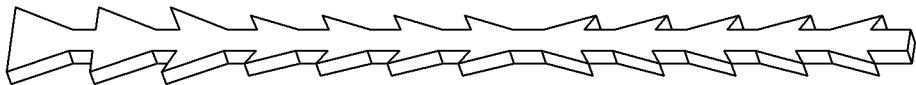
FIG. 10 is a perspective view of a form of the 3D thread according to the first example of the present disclosure.
Figure 11:
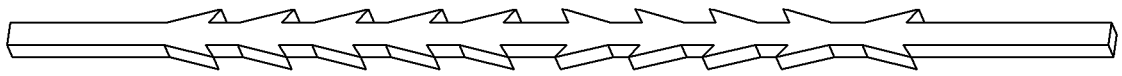
FIG. 11 is a perspective view of another form of the 3D thread according to the first example of the present disclosure.
Figure 12:
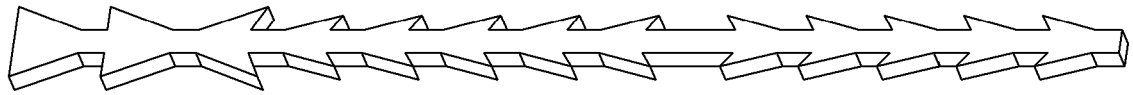
FIG. 12 is a perspective view of another form of the 3D thread according to the first example of the present disclosure.
Figure 13:
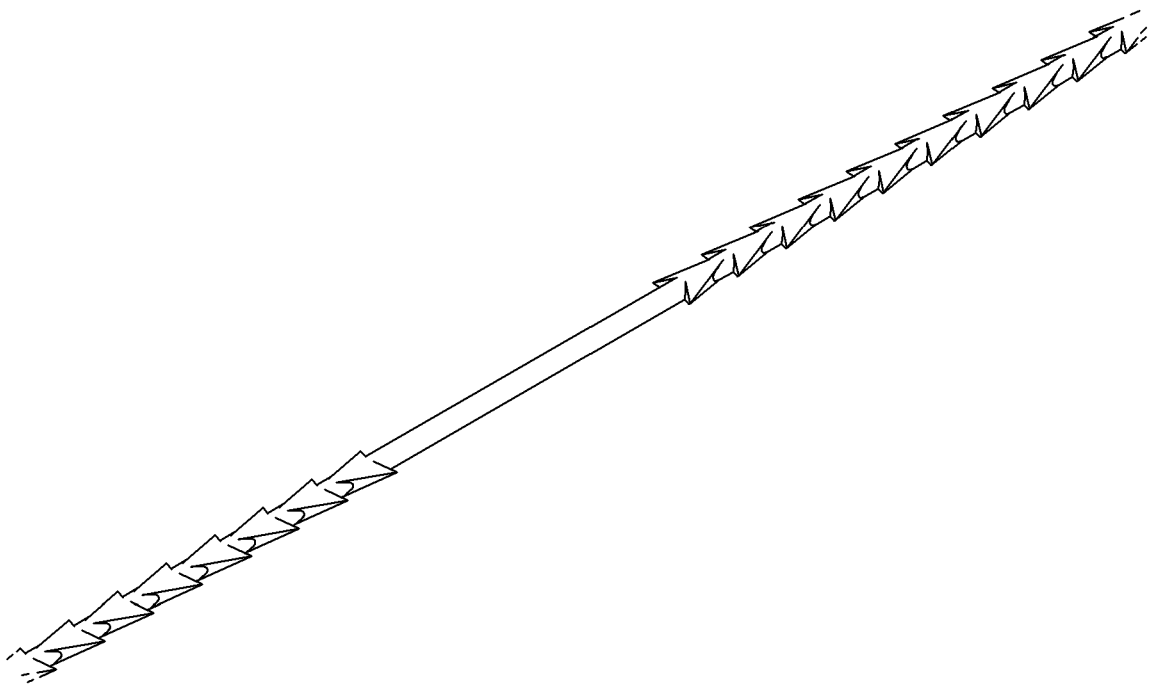
FIG. 13 is a perspective view of another form of the 3D thread according to the first example of the present disclosure.
Figure 14:
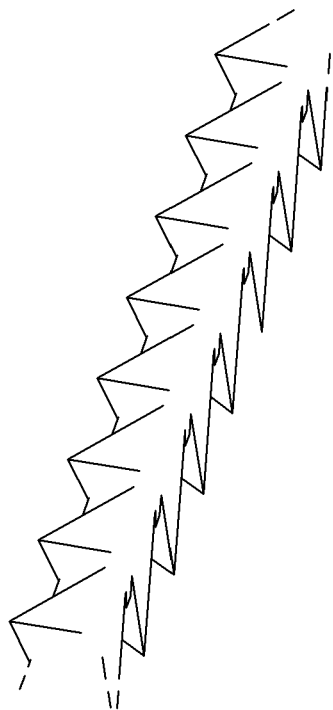
FIG. 14 is a perspective view of another form of the 3D thread according to the first example of the present disclosure.

FIG. 8 is a perspective view of a medical 3D thread according to an additional example of the present disclosure.

The medical 3D thread according to an additional example of the present disclosure has the same structure as the medical 3D thread according to the first example except that the first barb set 210 and the second barb set 220 have the longest oblique sides to face each other.

That is, in the medical 3D thread according to the first example, the barbs of the first barb set 210 and the second barb set 220 are formed heading toward the center part 110 and thus do not face each other, but in the medical 3D thread according to an additional example, barbs are formed in the opposite direction of the center part 110, so that the longest oblique sides of the respective barbs may be arranged to face each other.

Further, the center part 110 of the medical 3D thread according to an additional example may be formed shorter in length than that of the medical 3D thread according to the first example, and the medical 3D thread according to an additional example may not include the spare parts 120 on its both ends.

FIG. 9A through FIG. 9D are perspective views of a medical 3D thread according to an additional example of the present disclosure.

In the medical 3D thread according to an additional example of the present disclosure, the body part 100 and a barb part may have a semicircular longitudinal section.

That is, as shown in FIG. 9, the body part 100 may include barbs extended from both lateral sides. One of the other sides where barbs are not formed may be formed flat and the other side corresponding to the one flat side may be convexly curved.

The multiple barbs may have different widths from each other and may have a have a semicircular longitudinal section in the width direction. Each barb may have the greatest thickness in a portion adjacent to the body part and may decrease in thickness as being farther from the body part.

The longest oblique side of the barb may be curved by bending the angular portion of the barb in a direction in which the barb is formed.

That is, the barb is slightly curved in a direction toward which the barb extended from the body part heads, and, thus, the tensile force may be increased.

Further, even when the angular portion of the barb inserted into the skin is melted or damaged, the loss of the tensile force can be reduced since the barb increases in thickness from the angular portion toward the body part.

In the medical 3D thread according to an additional example of the present disclosure, the barb part and the body part may have different thicknesses. A conventional thread has been produced to have different width and length, but the medical 3D thread according to an additional example of the present disclosure may be produced to have different width, length, and thickness. The medical 3D thread according to an additional example may have the same structure as the medical 3D thread according to the first example, and each barb extended from the body part 100 may increase in thickness as being closer to the body part 100.

Hereafter, the actual size of the medical 3D thread according to the present disclosure will be described. The medical 3D thread according to each example of the present disclosure may include 6 to 10 barbs per unit length of 1 cm.

The medical 3D thread according to the present disclosure may include 8 barbs per cm and may include more barbs per cm than conventional medical 3D threads. Thus, the tensile force of the 3D thread may be increased.

FIG. 10 through FIG. 14 show examples of 3D threads modified in shape according to use with medical 3D threads according to present disclosure.

In producing medical 3D threads using ultrasonic waves as shown in the drawings, the above-described examples just show illustrative shapes, and the medical 3D threads can be produced in various shapes. Therefore, the present disclosure is not limited to the above-described examples.

Hereafter, a medical 3D thread produced using ultrasonic waves according to a second example of the present disclosure will be described in detail.

Figure 16:
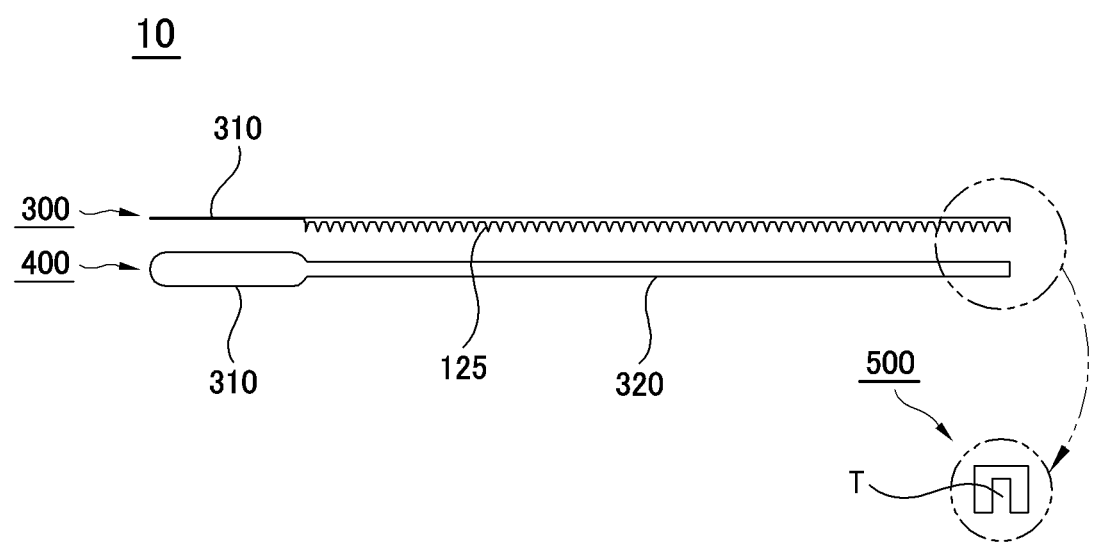
FIG. 16 shows a side view, a plan view, and a front view of a medical thread including a stop member (head part) according to second and third examples of the present disclosure.

FIG. 16 shows a medical thread having a trench shape according to an example of the present disclosure, and reference numeral 300 in FIG. 16 indicates a side view of a medical thread 10 according to an example of the present disclosure, reference numeral 400 in FIG. 16 indicates a plan view of the medical thread 10 according to an example of the present disclosure, and reference numeral 500 in FIG. 16 indicates a front view of the medical thread 10 according to an example of the present disclosure.

Referring to FIG. 16, the medical thread 10 having a trench shape according to an example of the present disclosure includes a body portion 320 including a trench T which is recessed in the middle of a lower surface in a long-side length direction, and multiple barb parts 125 formed and protruded from both sides of the body portion 320.

Therefore, when inserted into the inner layer of the skin, the medical thread 10 of the present disclosure has a large contact area with skin tissues due to the trench T of the body portion 320. Thus, it is possible to suppress the deviation or movement of the medical thread from where the medical thread is initially inserted and also possible to improve the fixation power with the skin tissues.

Hereafter, a medical thread of the present disclosure including a trench structure and multiple barbs that more effectively suppress the deviation of the medical thread from the skin tissues than conventional medical threads shown in FIG. 19 and FIG. 20 will be described in detail.

Figure 18:
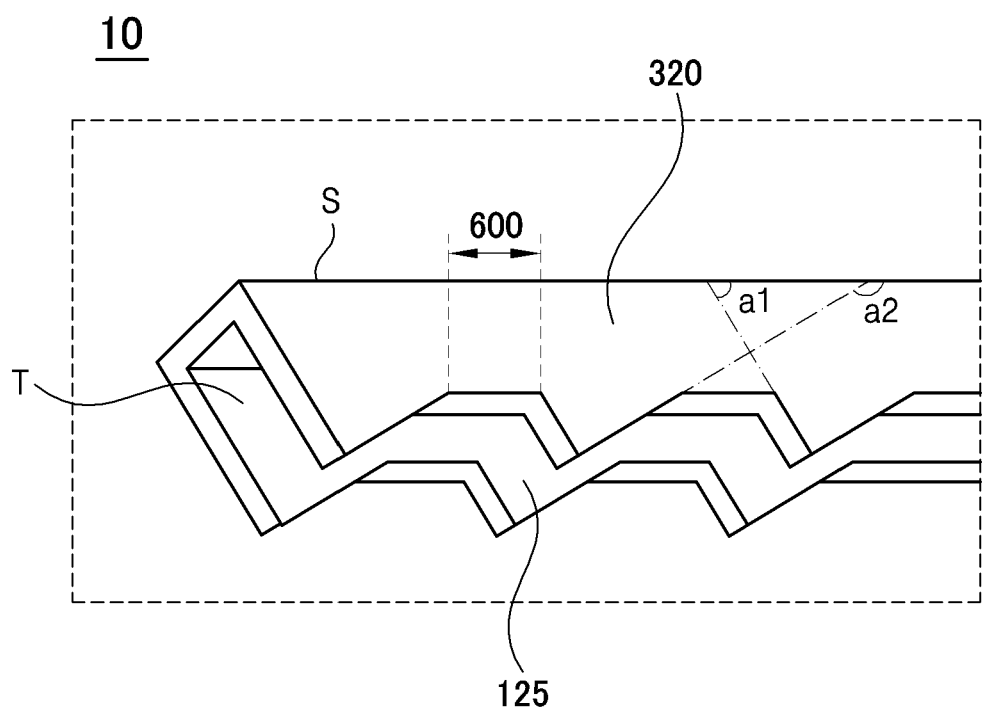
FIG. 18 is an enlarged view provided to explain a body portion and a barb part of the medical thread including the stop member (head part) according to the second and third examples shown in FIG. 16.

FIG. 18 is an enlarged view provided to explain a trench-shaped body portion and a barb part of the medical thread according to the present disclosure.

The medical thread 10 of the present disclosure may be formed of a biodegradable polymer (polymer material) such as co-polymers including polylactic acid, polydioxanone, lactic acid, and glycolic acid.

Desirably, a transverse section of the body portion 320 cut in a direction perpendicular to the long-side length direction may have a "E" shape, but is not limited thereto. For example, the transverse section of the body portion 320 may have a "C" shape.

Referring to FIG. 18, the multiple barb parts 125 may be formed to slant at a predetermined angle with respect to an upper surface S of the body portion 320. In this case, each of the barb parts 125 may have a pointed wedge shape. For example, as shown in FIG. 18, if the multiple barb parts 125 are formed to slant at an obtuse angle a2 with respect to the upper surface S, each of the barb parts 125 may be formed such that the pointed wedge shape slants toward the front of the body portion 320. The wedge portion located in front maintains the fixation power with the skin and thus may serve to pull the skin forward. Likewise, if the multiple barb parts 125 are formed to slant at an acute angle a1 with respect to the upper surface S, each of the barb parts 125 may be formed such that the pointed wedge shape slants toward the back (on the right side of FIG. 18) of the body portion 320 (not illustrated). The wedge portion located in the back maintains the fixation power with the skin and thus may serve to pull the skin backwards.

Further, one end of the body portion 320 may be formed to extend to the outermost barb part 125 among the multiple barb parts 125. Specifically, one end of the body portion 320 in the long-side length direction may be formed to slant downwards and extended to the outermost barb part 125. That is, as shown in FIG. 18, the final end of the body portion 320 is formed by extending the outermost barb part as it is, and, thus, the final end of the body portion 320 may be formed at a specific angle. One end of the body portion 320 may also slant in the same direction as the multiple barb parts 125 and thus strengthen one-directional tensile force of the medical thread 10.

The multiple barb parts 125 may be provided corresponding to each other on opposite sides of the trench T of the body portion 320. For example, the barb parts 125 may be protruded downwards from both wall surfaces of the trench T of the body portion 320 and formed to face each other at corresponding locations.

Herein, the bottom point of the trench T may be lower than points from which the multiple barb parts 125 start. Therefore, the bottom point of the trench T may have a greater depth than the bottom point of the trench T which is equal in depth to the points where the multiple barb parts 125 start. Thus, the body portion 320 can be embedded to a greater depth in the skin, which can improve the fixation power of the thread. Additionally, a space where a filler can be introduced may be formed in the trench T.

Further, the multiple barb parts 125 may be continuously formed at a distance along the long-side length direction of the body portion 320. For example, the barb parts 125 may be spaced apart at a predetermined distance 600 along the longitudinal direction of the body portion 320. In this case, the distance 600 between the barb parts 125 enables the barb parts 125 to be independently embedded in the skin. Thus, the fixation power of the medical thread 10 with the skin can be increased.

The medical thread 10 according to the present disclosure may be produced by ultrasonic processing. The ultrasonic processing facilitates precise processing which cannot be achieved by conventional molding or cutting and three-dimensional processing as shown in the trench-shaped medical thread 10 of the present disclosure. For example, the medical threads shown in FIG. 19 and FIG. 20 are produced by compressing yarn and pressing the compressed yarn in a mold and by cutting yarn to form barbs, respectively, and thus cannot have a delicate 3D trench structure as in the present disclosure.

The ultrasonic processing is known in the art as a process for precisely polishing a structure by supplying grinding particles between the structure and a tool that vibrates using ultrasonic vibration as an energy source. Therefore, further detailed description thereof will not be provided. Meanwhile, in order to produce the 3D thread of the present disclosure, a process of putting yarn in a mold having a specific 3D engraved or embossed pattern, scanning ultrasonic waves, and pressing the yarn may be performed in addition to the conventional ultrasonic processing.

Figure 15:
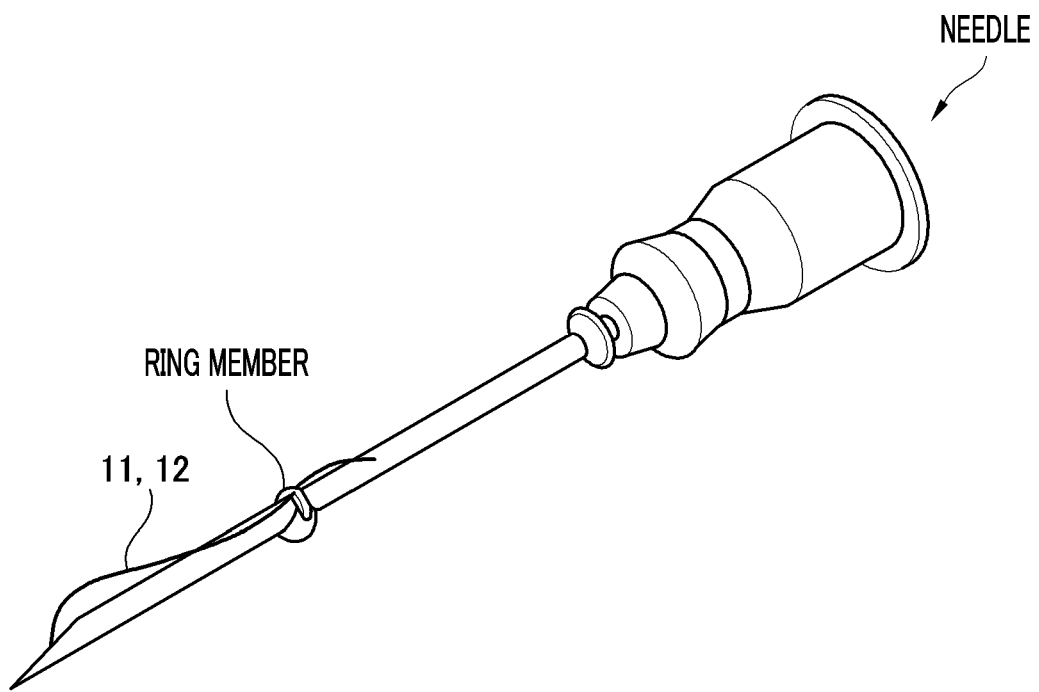
FIG. 15 shows a needle with a conventional medical thread.

Hereafter, the role of a stop member 310 of the present disclosure will be described in detail. FIG. 15 shows a needle with a conventional medical thread.

In general, a medical thread needs to be inserted into a needle tube of a syringe needle so as to be used for skin lifting.

Referring to FIG. 15, a conventional medical thread 11, 12 is inserted into a syringe needle and then, the inserted medical thread 11, 12 is hung over the syringe needle and fixed to the syringe needle by a ring member. That is, the medical thread 11, 12 needs to be inserted into the needle tube of the syringe needle and then further fixed to the needle using the ring member, which is time consuming.

Referring to FIG. 16 again, the medical thread 10 of the present disclosure includes the stop member 310 provided on one end of the body portion 320 and having a greater width than the body portion 320 when viewed from the top. In this case, the stop member 310 may be formed into a sheet shape, but is not limited thereto.

That is, when the medical thread 10 of the present disclosure is inserted into a needle tube of a needle, the stop member 310 formed on one end of the body portion 320 is stopped by a front end of the needle. Thus, a process of fixing the medical thread 10 to the needle using a separate ring member can be skipped. Therefore, it is possible to reduce time required to insert the medical thread into the needle tube of the syringe needle.

Hereafter, a medical 3D thread produced using ultrasonic waves according to a third example of the present disclosure will be described in detail.

The stop member denoted by reference numeral 310 will be referred to as "head part" of the medical 3D thread produced using ultrasonic waves according to the third example of the present disclosure.

FIG. 16 shows the medical thread including the head part according to the third example of the present disclosure, and reference numeral 300 in FIG. 16 indicates a side view of the medical thread 10 according to the third example of the present disclosure, reference numeral 400 in FIG. 16 indicates a plan view of the medical thread 10 according to the third example of the present disclosure, and reference numeral 500 in FIG. 16 indicates a front view of the medical thread 10 according to the third example of the present disclosure.

Figure 17:
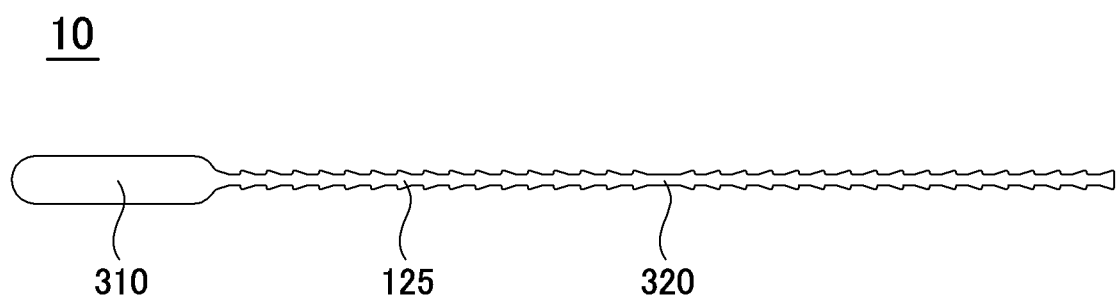
FIG. 17 is a plan view of a medical thread including a stop member (head part) according to an additional example of the second example of the present disclosure.
Figure 21:
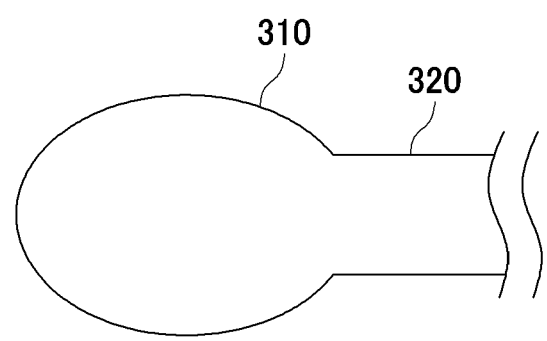
FIG. 21 is an enlarged view provided to explain a shape of the stop member (head part) according to the third example of the present disclosure.
Figure 22:
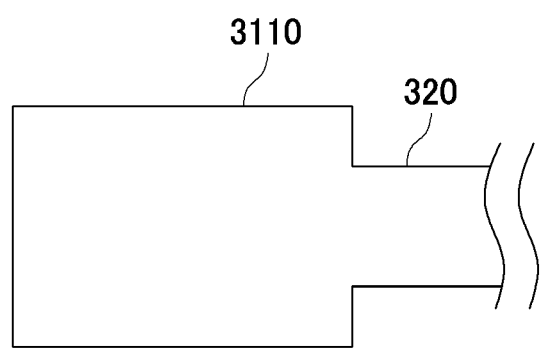
FIG. 22 is an enlarged view provided to explain another shape of the stop member (head part) according to the third example of the present disclosure.
Figure 23:
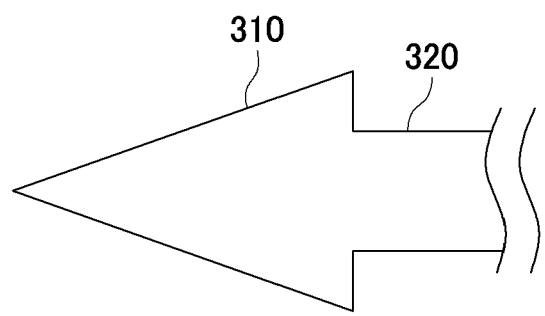
FIG. 23 is an enlarged view provided to explain another shape of the stop member (head part) according to the third example of the present disclosure.

FIG. 17 is a plan view of a medical thread including a head part according to another example of the present disclosure, and FIG. 21 through FIG. 23 are enlarged views provided to explain various shapes of the head part according to the third example of the present disclosure.

Referring to FIG. 16 and FIG. 17, the medical thread 10 of the present disclosure includes the body portion 320 extended in one direction, the head part 310 provided on one end of the body portion 320 and having a greater width than the body portion 320, and the multiple barb parts 125 formed and protruded from at least one side of the body portion 320.

Referring to FIG. 15 through FIG. 17, the head part 310 may have a length greater than the size of a hole of the needle where the medical thread 10 is inserted and kept. Thus, the medical thread 10 of the present disclosure is formed such that the body portion 320 of the medical thread 10 is first inserted into the needle and then the head part 310 is folded outside the needle, and, thus, the medical thread 10 can be fixed to the needle.

That is, the medical thread 10 of the present disclosure includes the head part 310 which has a width greater than the size of the hole of the needle and is folded toward a lower end of the needle when being stopped by the front end of the needle, and, thus, the medical thread 10 can be fixed outside the needle. Therefore, a process of fixing the medical thread to the needle using a separate ring member can be skipped.

Also, it is possible to reduce time required to insert the medical thread into the needle tube of the syringe needle.

The medical thread 10 of the present disclosure includes the head part 310, the body portion 320, and the multiple barb parts 125. For example, the multiple barb parts 125 may be formed and protruded from at least one side of the body portion 320 extended in one direction. The multiple barb parts 125 serve to suppress the movement of the medical thread 10 in the skin after surgery for insertion of the medical thread 10 into the human skin is completed. The shapes of the body portion 320 and the barb parts 125 will be described in detail later.

Referring to FIG. 17, the head part 310 may be formed into a quadrangular shape with rounded corners having certain curvatures. Thus, the head part 310 can be folded outside the needle more safely than the head part 310 having a quadrangular shape with right-angled corners.

Further, the body portion 320 may have a three-dimensional shape and the head part 310 may have a sheet shape. More specifically, the head part 310 may have a different thickness from the body portion 320 and may have a smaller thickness than the body portion 320.

Furthermore, the head part 310 may have a smaller length than the body portion 320. Desirably, the head part 310 may have a length of 5 mm and the body portion 320 may have a length of form 22 mm to 40 mm. However, this is just an example and the head part 310 and the body portion 320 may have different lengths.

For example, referring to FIG. 21 through FIG. 23, the head part 310 may be formed into various shapes such as circular shape, oval shape, quadrangular shape, triangular shape, and the like. Specifically, as shown in FIG. 21, the head part 310 may be formed into a circular shape, but is not limited thereto and may also be formed into an oval shape. Also, as shown in FIG. 22, the head part 310 may be formed into a square shape, but is not limited thereto and may also be formed into a rectangular shape or a trapezoidal shape. Further, as shown in FIG. 23, the head part 310 may be formed into a triangular shape.

The head part of the medical thread according to the third example of the present disclosure may be formed by performing ultrasonic processing to yarn. More specifically, yarn may be inserted between an ultrasonic generator and a mold base in which a sheet shape is engraved and ultrasonic processing may be performed to the yarn, so that one end of the yarn may be pressed into the sheet shape. The one end of the yarn which has been pressed into the sheet shape may serve as the head part 310 of the medical thread and has substantially the same cross-sectional area as the body portion 320 but has a cross-sectional width which is too long to be inserted into the needle. That is, the head part is formed by performing ultrasonic processing to one end of the yarn and has a long width of a cross-section (cut perpendicular to the long-side length direction of the body portion) so as to cover a cutting portion of the needle and a small thickness so as not to irritate the tissues when it is inserted under the skin. Since the head part 310 is formed by performing ultrasonic processing to one end of the yarn, the material of the yarn is not degraded, and, thus, the material properties, such as strength and flexibility, of the head part 310 can be maintained similar to those of the body portion 320. Therefore, the ease of assembly can be secured and the tissues can be protected against the cutting portion of the needle while the absorption into the living tissues or the bearing power can be maintained appropriately. The medical thread 10 may be inserted into the needle from the body portion 320 and the head part 310 may be folded outside the needle and may cover the cutting portion on the front end of the needle. With this configuration, the medical thread 10 can be fixed to the needle and can also protect the tissues against the cutting portion when the needle is inserted into the tissues.

Hereafter, various shapes of the body portion and the barb parts of the medical thread including the head part of the present disclosure will be described with reference to FIG. 16 through FIG. 20.

Figure 19:
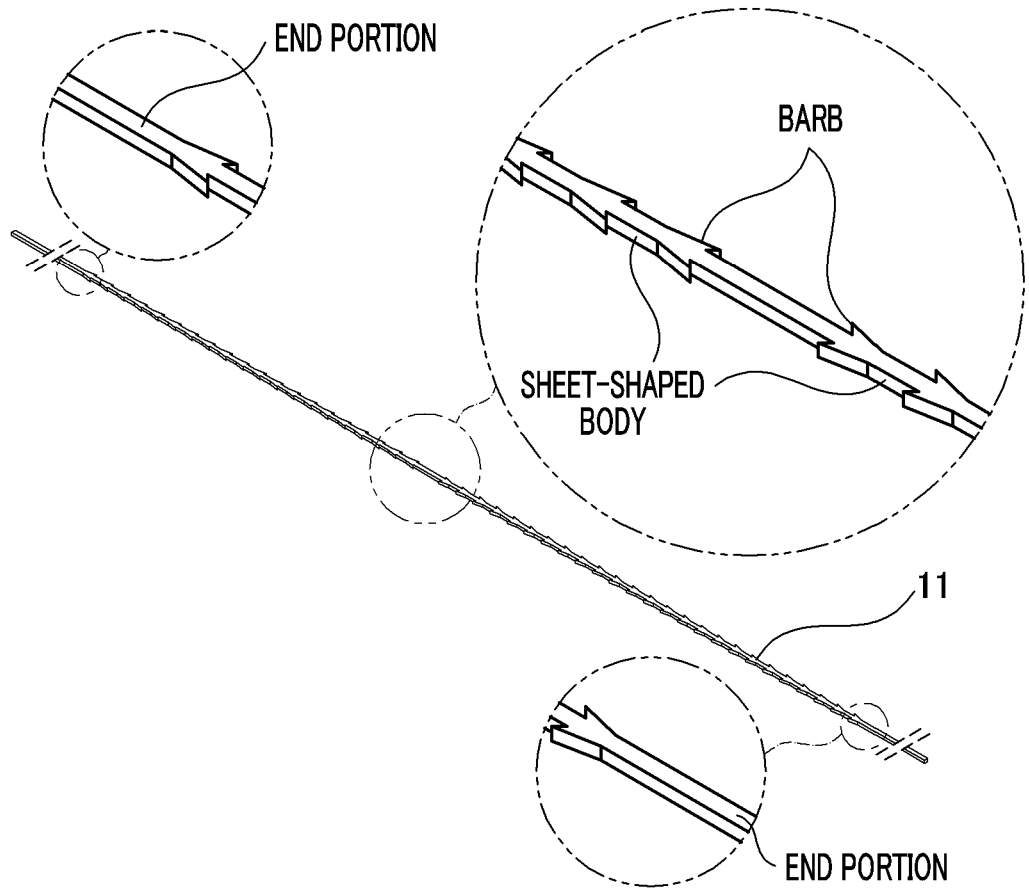
FIG. 19 shows a conventional medical thread produced using a mold.
Figure 20:
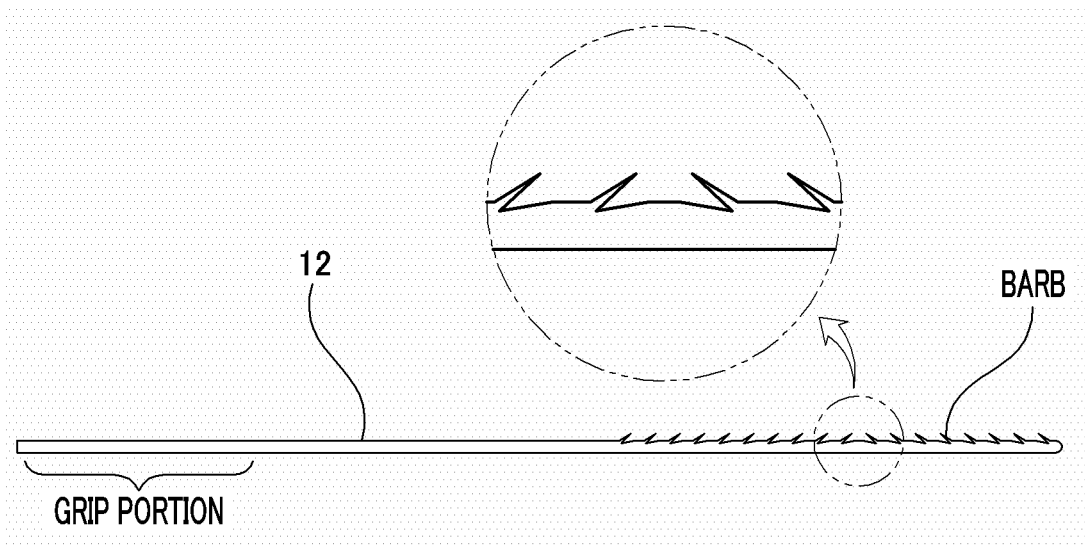
FIG. 20 shows a conventional medical thread produced by cutting.

FIG. 18 is an enlarged view provided to explain a body portion and a barb part of the medical thread including the head part shown in FIG. 16, FIG. 19 shows a conventional medical thread produced using a mold, and FIG. 20 shows a conventional medical thread produced by cutting.

Typical methods of forming barbs on a medical thread may include a method of manually forming barbs using the blade of a knife, a mechanical method of forming barbs using a machine equipped with the blade of a knife, and a method of forming barbs by compressing a medical thread.

As shown in FIG. 19, in the case of a compression method using a mold, a source material of a medical thread 11 may be heated at a predetermined temperature and the heated source material of the medical thread 11 may be compressed to form prickly barbs on the surface. According to this compression method, the shape of the medical thread is changed. Therefore, it is difficult to insert the medical thread into a needle, and, thus, a needle having a large diameter needs to be used and a contact area with the skin tissues is decreased due to a sheet-shaped body.

As shown in FIG. 20, in the case of a cutting method, barbs are formed by cutting the surface of a medical thread 12. Thus, the size and the thickness of the barbs may be limited. Further, the barbs have excessively sharp ends and thus may stimulate the surrounding tissues and nerves. Also, the strength of the medical thread 12 is greatly decreased due to damage to the medical thread 12 caused by cutting. Furthermore, bioabsorption of the relatively thin barbs may be carried out rapidly in the body, and, thus, the fixation power with the skin tissues can be easily lost.

To solve the above-described problems, the medical thread 10 including the head part 310 of the present disclosure may be produced to have a three-dimensional structure by ultrasonic processing.

For example, as shown in FIG. 16, the medical thread 10 of the present disclosure may be formed including the body portion 320 including the trench T which is recessed in the middle of the lower surface in the long-side length direction, and the multiple barb parts 125 formed and protruded from both sides of the trench T. For another example, as shown in FIG. 17, the medical thread 10 of the present disclosure may be formed including the body portion 320 extended in one direction and the multiple barb parts 125 formed at corresponding locations in the long-side length direction of the body portion 320.

Referring to FIG. 17, the medical thread 10 of the present disclosure includes the body portion 320 extended in one direction, the multiple barb parts 125 formed at corresponding locations in the long-side length direction of the body portion 320, and the head part 310 provided on one end of the body portion 320 and having a greater width than the body portion 320 when viewed from the top.

Referring to FIG. 16 and FIG. 18, the medical thread 10 according to the third example of the present disclosure includes the body portion 320 including the trench T which is recessed upwards in the middle of the lower surface in the long-side length direction, the multiple barb parts 125 formed and protruded downwards from both sides of the body portion 320, and the head part 310 provided on one end of the body portion 320 and having a greater width than the body portion 320 when viewed from the top. Desirably, the body portion 320 may have a "⊏"-shaped transverse section, but is not limited thereto. For example, the body portion 320 may have a "C"-shaped transverse section or may be recessed in the middle of the lower surface.

For example, the medical thread 10 may be formed of a biodegradable polymer (polymer material) such as co-polymers including polylactic acid, polydioxanone, lactic acid, and glycolic acid.

For example, referring to FIG. 17 and FIG. 18, the multiple barb parts 125 may be formed symmetrical to each other at a predetermined distance and may be formed into arrow shapes facing each other based on half the length of the long side of the body portion 320. For another example, the multiple barb parts 125 may be formed to slant at a predetermined angle with respect to an outer surface of the body portion 320. In this case, each of the barb parts 125 may have a pointed wedge shape. That is, the multiple barb parts 125 formed to slant at a predetermined angle serve to pull the skin in one direction and thus improve skin lifting.

Further, one end of the body portion 320 may be formed to extend to the outermost barb part 125 among the multiple barb parts 125. Specifically, one end of the body portion 320 in may be formed to slant downwards and extended to the outermost barb part 125. That is, as shown in FIG. 18, the final end of the body portion 320 is formed by extending the outermost barb part as it is, and, thus, the final end of the body portion 320 may be formed at a specific angle. One end of the body portion 320 may also slant in the same direction as the multiple barb parts 125 and thus strengthen one-directional tensile force of the medical thread 10.

The multiple barb parts 125 may be provided corresponding to each other on opposite lower sides of the trench T of the body portion 320. For example, the barb parts 125 may be protruded downwards from both wall surfaces of the trench T of the body portion 320 and formed to face each other at corresponding locations. Herein, the bottom point of the trench T may be lower than points from which the multiple barb parts 125 start. Therefore, the bottom point of the trench T may have a greater depth than the bottom point of the trench T which is equal in depth to the points where the multiple barb parts 125 start. Thus, the body portion 320 can be embedded to a greater depth in the skin, which can improve the fixation power of the thread.

Further, the multiple barb parts 125 may be continuously formed at a distance along the longitudinal direction of the body portion 320. For example, the barb parts 125 may be spaced apart at the predetermined distance 600 along the longitudinal direction of the body portion 320. In this case, the distance 600 between the barb parts 125 enables the barb parts 125 to be independently embedded in the skin. Thus, the fixation power of the medical thread 10 with the skin can be increased.

Therefore, when inserted into the inner layer of the skin, the medical thread 10 of the present disclosure has a large contact area with skin tissues due to the trench T of the body portion 320 and the barb parts 125. Thus, it is possible to suppress the deviation or movement of the medical thread from where the medical thread is initially inserted and also possible to improve the fixation power with the skin tissues.

The 3D thread according to the present disclosure can be produced only by ultrasonic processing. In a conventional method, a medical thread is produced by compressing yarn and pressing the yarn in a mold or cutting yarn to form barbs. Therefore, it is impossible to produce a delicate 3D structure provided by the present disclosure. The ultrasonic processing is known in the art as a process for precisely polishing a structure by supplying grinding particles between the structure and a tool that vibrates using ultrasonic vibration as an energy source. Therefore, further detailed description thereof will not be provided.

Meanwhile, in order to produce the 3D thread of the present disclosure, a process of putting yarn in a mold having a specific 3D engraved or embossed pattern, scanning ultrasonic waves, and pressing the yarn may be performed in addition to the conventional ultrasonic processing. Therefore, precise processing which cannot be achieved by conventional molding or cutting can be performed and a delicate three-dimensional shape as shown in the trench-shaped medical thread 10 can be formed.

Specifically, the 3D thread produced by the method of the present disclosure and a 3D thread produced according to conventional technology can be compared as follows. The 3D thread of the present disclosure can be very delicately produced using ultrasonic waves and thus may have a smaller and more delicate pattern than the 3D thread produced according to conventional technology.

The above description of the present disclosure is provided for the purpose of illustration, and it would be understood by a person with ordinary skill in the art that various changes and modifications may be made without changing technical conception and essential features of the present disclosure. Thus, it is clear that the above-described embodiments are illustrative in all aspects and do not limit the present disclosure. For example, each component described to be of a single type can be implemented in a distributed manner. Likewise, components described to be distributed can be implemented in a combined manner.

The scope of the present disclosure is defined by the following claims rather than by the detailed description of the embodiment. It shall be understood that all modifications and embodiments conceived from the meaning and scope of the claims and their equivalents are included in the scope of the present disclosure.

I claim:

1. A medical thread, comprising:
   a body part which serves as a central axis of the medical thread; and
   multiple barb parts formed and extended from both lateral sides of the body part,
   wherein barbs of the multiple barb parts have different widths,
   wherein the multiple barb parts comprise a first barb set including first barb parts formed in one direction and a second barb set including second barb parts formed in the opposite direction of barb parts of the first barb parts and spaced apart from the first barb set, and a 1st-1st barb part and a 2nd-1st barb part formed at both sides of the body part with the first and second barb sets interposed therebetween,
   wherein the 1st-1st barb part formed in a direction adjacent to the first barb set is formed in a direction opposite to the first barb parts, and the 2nd-1st barb part formed in a direction adjacent to the second barb set is formed in an opposite direction to the second barb parts,
   wherein the body part is configured so that there are no barb parts from the 1st-1st barb part to one end of the body part and there are no barb parts from the 2nd-1st barb part to an other end of the body part,
   wherein one of the 1st-1st barb part and the 2nd-1st barb part is formed differently from the other of the 1st-1st barb part and the 2nd-1st barb part in at least one of a width, a shape, and a thickness,
   wherein the 1st-1st barb part is formed in the direction heading toward a center part of the body part connecting the first barb set and the second barb set,
   wherein a thickness of the 1st-1st barb part is the same as a thickness of the body part, and
   wherein the medical thread is produced by applying ultrasonic waves to a yarn.

2. The medical thread of claim 1,
   wherein the yarn for producing the thread is thermoplastic resin, and the ultrasonic waves used for producing the medical thread have a frequency of from 2 kHz to 4 kHz, and the medical thread is produced by inserting the yarn between an ultrasonic generator and a mold base in which an engraved pattern is formed and compressing the yarn.

3. The medical thread of claim 1,
   wherein if a length direction of the body part is defined as a transverse direction and a width direction of the body part is defined as a longitudinal direction, a transverse section or longitudinal section of each barb part has a rectangular shape.

4. The medical thread of claim 3,
   wherein an angular portion of the barb part has a predetermined thickness.

5. The medical thread of claim 1,
   wherein the 2nd-1st barb part is formed in the direction heading toward the center part.

6. The medical thread of claim 1,
   wherein the yarn is made of materials including Polydioxanone (PDO).

* * * * *